United States Patent [19]

Namba et al.

[11] Patent Number: 4,622,208

[45] Date of Patent: Nov. 11, 1986

[54] OPTICAL CONTINUOUS MEASURING APPARATUS FOR REACTION-LIQUID

[75] Inventors: Yuzaburo Namba, Yatabe; Toshio Takahashi, Honjo, both of Japan

[73] Assignee: Eisai Co., Ltd., Tokyo, Japan

[21] Appl. No.: 730,035

[22] Filed: May 3, 1985

[30] Foreign Application Priority Data

May 11, 1984 [JP] Japan ................................ 59-94244

[51] Int. Cl.⁴ ...................... G01N 21/05; G01N 35/06
[52] U.S. Cl. .................................. 422/65; 73/864.81; 141/67; 356/246; 422/63; 422/100; 422/102; 436/47; 436/180
[58] Field of Search .................. 422/63, 64, 65, 67, 422/100, 102; 73/864.81; 141/67; 356/246

[56] References Cited

U.S. PATENT DOCUMENTS

| | | | |
|---|---|---|---|
| 3,614,434 | 10/1971 | Horwitz et al. | 422/64 |
| 3,622,279 | 11/1971 | Moran | 422/65 |
| 4,129,419 | 12/1978 | Hermann, Jr. | 422/64 |
| 4,478,094 | 10/1984 | Salomaa et al. | 422/65 |

Primary Examiner—Michael S. Marcus
Attorney, Agent, or Firm—Murray and Whisenhunt

[57] ABSTRACT

An optical continuous measuring apparatus for a reaction-liquid comprises: a microplate provided with a plurality of microcups arranged on a straight line at intervals of a certain distance; a rotary disc provided over the microplate so as to be rotatable, which disc is provided with suction nozzles in its outer periphery, which nozzles are sequentially inserted into the microcups upon rotation of the disc, and also provided with transparent measuring cells communicating therewith inward in radial direction of the disc; suction means for sucking the reaction-liquid received in the microcups from the microcups into the measuring cells through the suction nozzles when the suction nozzles of the rotary disc are inserted into the microcups; an optical measuring means for measuring the reaction-liquid received in the measuring cells; a supplying means for supplying a rinsing liquid to the measuring cells; and a discharging means for discharging the reaction-liquid and the rinsing liquid from the measuring cells.

7 Claims, 13 Drawing Figures

OPTICAL CONTINUOUS MEASURING APPARATUS FOR REACTION-LIQUID

BACKGROUND OF THE INVENTION

1. Field of the Invention

The present invention relates to an optical continuous and automatic measuring apparatus for various kinds of reaction-liquids received in a plurality of microcups which are provided at intervals of a certain distance in a microplate.

2. Description of the Prior Art

Hitherto, in a biochemical inspection of a blood specimen, a urine specimen and the like, and in an immunoreaction and so on, for example, Japanese Patent Publication No. 13907/1981 discloses an optical continuous and automatic measuring apparatus for the various kinds of the reaction-liquids received in the microcups, in which apparatus, the microplate is made of a transparent material and horizontally transferred to be measured by being subjected to the light beam which is issued from a light source provided under the microplate so as to be directed upward to the bottom surface of the microcups so that the light beam having passed through the microcups is received by a light detector provided over the microplate to perform the measurement of such liquids.

However, in such a type of the conventional measuring apparatus, it is not possible to use a microplate made of an opaque material, and furthermore, even if the microplate is made of a transparent material, there are various defects, for example, a defect that it is not possible to set a desirable length of optical path of the light beam because of the measured value varying on the same reactionliquid with every change of transparency due to differences in material properties and material thickness of the microplate and further because of a depth of the reaction-liquid received in the microcup itself being equal to a light traveling distance, i.e., a length of the optical path.

SUMMARY OF THE INVENTION

Consequently, it is an object of the present invention to provide an optical measuring apparatus which can eliminate the defects inherent in the conventional measuring apparatus, and in which apparatus of the present invention the microplate can be made of an opaque material and further there is no fear that the measured value varies on the same reaction-liquid with every change of transparency due to differences in material properties and material thickness of the microplate, and furthermore it is possible to automatically conduct a highly accurate measurement in a short time by using an accurate length of the optical path of the light beam irrespective of an amount of the reaction-liquid received in the microcup, so that the measurement operation is simplified according to the present invention.

The above object of the present invention is accomplished by providing an optical measuring apparatus characterized by comprising: a plate-like member provided with a plurality of cavities for receiving a reaction-liquid, which cavities are arranged on a straight line at intervals of a certain distance; a first driving mechanism for intermittently transferring the plate-like member by the certain distance of the interval of the plurality of cavities on its each transferring movement in a direction in which the plurality of cavities are linearly arranged; a rotary member provided over the plate-like member so as to be rotatable in the direction in which the plurality of the cavities are linearly arranged; a plurality of suction nozzles the number of which is identical with that of the cavities, which nozzles are so arranged that they radially project outward from an outer periphery of the rotary member to have their front ends circumferentially spaced a prescribed distance apart from each other, which prescribed distance is substantially equal to or slightly greater than the interval of the plurality of the cavities of the plate-like member; a plurality of measuring cells made of a transparent material and radially disposed on the rotary member, which cells communicates with each of the plurality of the suction nozzles and forms a discharging opening; a second driving mechanism for intermittently rotating the rotary member by a distance substantially equal to the certain distance of the interval of the plurality of the cavities upon its each rotating movement; a suction member giving a negative pressure to the opening of each of the plurality of the measuring cells when each of the suction nozzles is inserted into each of the cavities of the plate-like member; a measuring member for optically measuring the reaction-liquid received in the measuring cell, which measuring member is disposed behind the suction member in a direction in which the measuring cells are transferred; and a rinsing liquid supplying/discharging member for supplying a rinsing liquid to the measuring cells and discharging the same from the measuring cells, which rinsing liquid supplying/discharging member is disposed behind the measuring member in the direction in which the measuring cells are transferred.

In the above measuring apparatus of the present invention, the transferring movement of the plate-like memberis synchronized with the rotating movement of the rotary member so that the suction nozzles are sequentially inserted into the reaction-liquids received in the cavities formed on the surface of the plate-like member. In a position in which the suction nozzles are inserted in the cavities of the plate-like member, the suction member gives the measuring cells the negative pressure to automatically suck the reaction-liquids from the cavities of the platelike member into the measuring cells so that the reactionliquids are retained in the measuring cells. Then, the measuring cells are brought into a measuring position in which the reaction-liquids received in the transparent measuring cells is automatically measured. After such measurements of the reaction-liquids received in the measuring cells are finished, the measuring cells are brought into a rinsing position in which the rinsing liquid is supplied into each of the measuring cells by the rinsing liquid supplying/discharging member to rinse the inside thereof, so that the rinsing liquid is discharged together with the reaction-liquids form the measuring cells by the rinsing liquid supplying/discharging member, whereby the measurements are performed with the use of an accurate length of the optical path of the light beam irrespective of the variation of the amount of the reaction-liquid received in the measuring cell, and further such measurement does not require any man power at all and is performed in a short time.

In an embodiment of the present invention: the opening of the measuring cell opens to the side surface of the rotary member; the suction member comprises a suction passage provided in a supporting plate which has its side surface hermetically brought into slidable contact with a side surface of the rotary member, which suction passage has two openings one of which opens to a position communicating with the opening of the measuring cell and the other of which two openings opens to another position communicating with the suction pipe connected to a negative pressure source; and the rinsing liquid supplying/discharging member comprises a rinsing liquid supplying pipe communicating with a front end of the suction nozzle, a liquid discharging passage and a liquid discharging pipe both provided in the supporting member, which liquid discharging passage has two openings one of which opens to a position communicating with the opening of the measuring cell and the other of which two openings opens to another position communicating with the liquid discharging pipe.

Further, the above embodiment of the present invention is characterized in that: the rinsing liquid supplying pipe is provided with a slit in its front end, which slit has a sufficient width to enable the suction nozzle to pass through the slit when the suction nozzle is transferred in the rotational direction of the rotary member, so that the rinsing liquid retained in this slit under the effect of the surface tention of the rinsing liquid is introduced into the suction nozzle and the measuring cell to rinse both the inside and the outside of the suction nozzle and the inside of the measuring cell.

Further, another embodiment of the present invention is characterized in that: the opening of the liquid discharging passage, which opening communicates with the opening of the measuring cell, is constructed of an arcshaped opening formed in the side surface of the supporting member so that a discharging operation of the reactionliquid is started just before starting a supplying operation of the rinsing liquid to the measuring cell and a discharging operation of the rinsing liquid supplied in the measuring cell is continued after the measuring cell passed its rinsing position to make it possible that the liquid received in the measuring cell is completely discharged.

Further, another embodiment of the present invention is characterized in that: the plate-like member is movable in reciprocating manner in both its longitudinal and transverse directions; and the suction nozzles are provided in a portion of the outer periphery of the rotary member, wherein, in case that the plate-like member is under its returning movement, the suction nozzles do not abut against the plate-like member so that the returning movement of the plate-like member is free from the suction nozzles.

Further, another embodiment of the present invention is characterized in that: a front end of a connecting portion of the suction nozzle to the measuring cell is inserted into the measuring cell, in the vicinity of which front end are provided a plurality of through-holes which are circumferentially spaced a suitable distance apart from each other, so that the reaction-liquid is prevented from being transferred directly to a discharging opening of the measuring cell, i.e., prevented from being directly passed through the measuring cell without being filled in the measuring cell and so that the rinsing operation is sufficiently performed.

DETAILED DESCRIPTION OF THE PREFERRED EMBODIMENTS

In the drawings, the numeral 1 designates a microplate, on a surface of which a plurality of microcups 2 are uniformly formed at intervals of a certain distance P in both longitudinal and transverse directions thereof.

Figure 1:
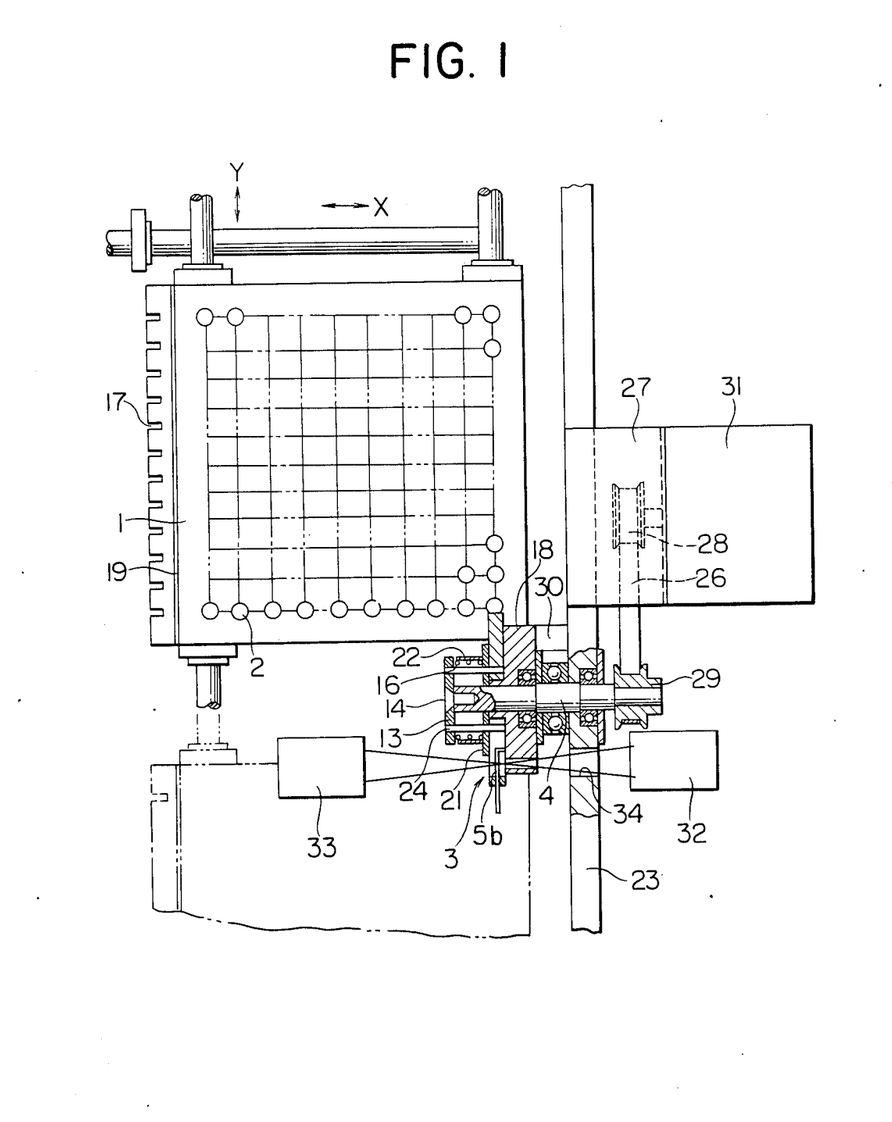
FIG. 1 is a partially cut away plan view of an embodiment of the optical continuous measuring apparatus for the reaction-liquid according to the present invention.

Such microplate 1 is placed on a table 19 as shown in FIG. 1, which table 19 is intermittently moved in both directions X and Y by the distance P upon its each intermittent movement. The numeral 17 designates a slit for positioning the microplate 1 when the microplate 1 is transferred in the direction Y to be stopped at a certain position.

A stationarily fixed plate 23 is provided alongside the microplate 1 in its transferring direction Y, parallel to which plate 23 and spaced a certain distance apart therefrom is procided a supporting plate 18. A rotary shaft 4 is rotatably supported by both the plates 18, 23 so as to be perpendicular to these plates 18, 23. A washer plate 13 is fixed to an end of the rotary shaft 4 by screws 14, which end exists in a side in which the microplate 1 exits. A disc 3 is mounted in place by means of stopper pins 24 which are mounted on the washer plate 13. A spring 16 is interposed between the washer plate 13 and a protecting plate 21 which is adjacent to the disc 3, so that the disc 3 is closely abutted against the supporting plate 18 through the protecting plate 21 and is rotated under such condition. The numeral 22 designates a cover for the spring 16. A pulley 29 is mounted on the other end of the rotary shaft 4, which end is opposite to the end to which the washer plate 13 is fixed. A detailed construction of the disc 3 is the same as that of another embodiment of the disc 3, shown in FIGS. 2 and 3, and therefore will be described later.

As shown in FIG. 1, a mounting plate 27 is mounted on the fixed plate 23, on which mounting plate 27 a stepping motor 31 is mounted. A pulley 28 is mounted on a rotary shaft of the stepping motor 31. A belt 26 runs around the the pulleys 28 and 29, so that the rotational movement of the disc 3 is synchronized with the intermittent transferring movement of the microplate 1 in its direction Y to be intermittently produced by actuation of the stepping motor 31. The numeral 30 designates a supporting post for supporting the plates 18, 23. The numerals 32 and 33 designate a light source and a light detector, respectively. As shown in FIG. 1, the light source 32 and the light detector 33 are so arranged that, when the measuring cell 5 is placed in a position 5b, the measuring cell 5 is interposed therebetween, whereby a light beam issued from the light source 32 passes through an opening 34 of the fixed plate 23 to be projected on the measuring cell 5 and the reaction-liquid therein. Thereafter, the light beam having passed through the reaction-liquid and the measuring cell 5 is received by the light detector 33 so that components of the thus obtained light beam are measured by a measuring/recording device (not shown).

Figure 2:
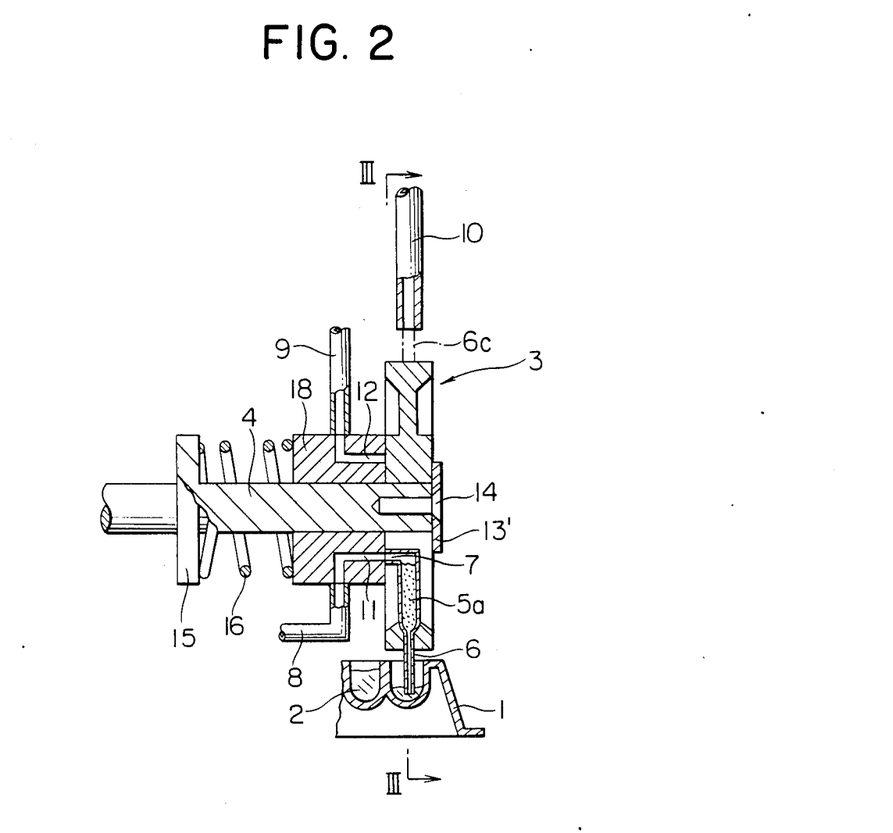
FIG. 2 is a partially longitudinally sectional front view of a modification of the essential parts of the above embodiment shown in FIG. 1.
Figure 3:
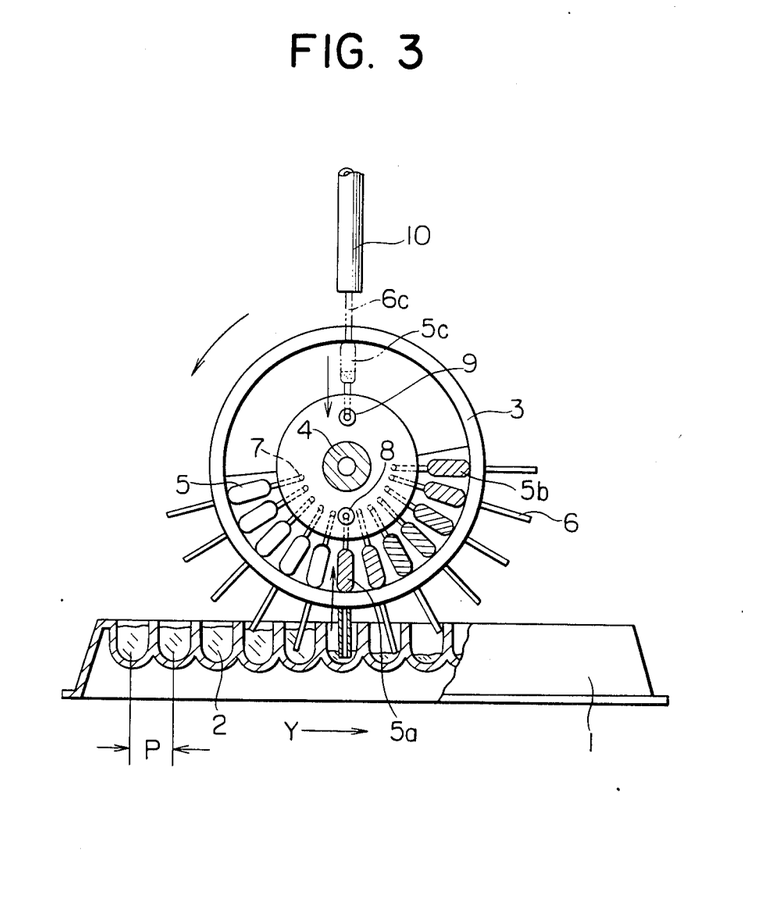
FIG. 3 is a partially sectional view taken along the line III—III of FIG. 2, shown in a direction of arrows thereof.

With reference to FIGS. 2 and 3, the disc 3 will be hereinafter described:

In a half of the disc 3 are radially disposed a plurality of transparent measuring cells 5 the number of which is identical with that of the microcups 2 existing on a straight line in the transverse direction Y of the microplate 1, which measuring cells 5 communicate with the suction nozzles 6 which are provided in the disc 3 so as to project radially outward from the outer periphery of the disc 3. The circumferential interval of a distance between outer ends of the individual suction nozzles 6 is substantially identical with or slightly greater than the distance P between the individual mircocups 2 in the straight line of the microplate 1. At a radially inner end of each of the measuring cells 5 is provided a discharging opening 7 directed to the rotary shaft 4. In the supporting plate 18, there are provided a liquid discharging passage 12 and a suction passage 11 consisting of a radial passage portion and an axial passage portion, which radial passage portion has an opening in its outer most end in a vertical direction along one of diameters of the supporting plate 18, which axial passage portion communicates with this radial passage portion and has its opening faced the discharging opening 7, to the outermost opening of which radial passage portion of the suction passage 11 is connected a suction pipe 8 or a liquid discharging pipe 9. A rinsing liquid supplying pipe 10 is provided so as to be directed downward in a position above the disc 3, in which position the pipe 10 communicates with the suction nozzle 6. The washer plate 13' of the embodiment of the present invention, shown in FIGS. 2 and 3 is smaller in diameter than the washer plate 13 of the embodiment of the present invention, shown in FIG. 1. In the embodiment shown in FIGS. 2 and 3, the rotary shaft 4 is provided with a flange 15, between which flange 15 and the supporting plate 18 is interposed the spring 16, so that this embodiment is simplified in its construction to be distinguished from the embodiment shown in FIG. 1 in this respect.

In measuring the reaction-liquid with the use of the measuring apparatus of the present invention having the above construction, the microplate 1, in the microcups 2 of which the reaction-liquid has been received, is intermittently transferred in the direction Y shown in FIGS. 1 and 3 by the distance P upon each intermittent movement of the microplate 1 by means of the driving mechanism (not shown), while the rotational movement of the disc 3 is synchronized with such intermittent transferring movement of the microplate 1 to be continued by the distance P each time it is produced by actuation of the stepping motor 31 in a direction shown by an arrow in FIG. 3.

Thereby, when the suction nozzle 6 of the measuring cell 5 is inserted into the microcups 2 of the microplate 1 and brought into a sucking position 5a as shown in FIG. 3, the discharging oepning 7 of the upper portion of the measuring cell 5 is coincident with the opening of the suction passage 11 of the supporting plate 18. Since the negative pressure is always given to the suction passage 11 through the suction pipe 8, the reaction-liquid received in the microcup 2 is sucked into the measuring cell 5 at the sucking position 5a as shown in FIG. 2, and then such measuring cell 5 is sequentially transferred into the measuring position 5b in which the light beam is projected on the measuring cell 5 from the light source 32 while the measuring cell 5 stays stationary in the measuring position 5b as shown in FIG. 3. On the basis of an amount of the light beam, which is thus projected on the measuring cell 5 and the reaction-liquid therein and passed therethrough to be received by the light detector 33, the reaction-liquid is measured and further recorded by a measuring instrument (not shown).

When the thus measured measuring cell 5 in its contents is further transferred to reach a rinsing position 5C as shown in FIG. 3, the suction nozzle 6 connected to such measuring cell 5 is brought into a position 6C as shown with a chain-line in FIG. 3, so that the opening of the suction nozzle 6 communicates with the rinsing liquid supplying pipe 10, whereby the rinsing liquid is supplied from the supplying pipe 10 to the suction nozzle 6 in the position 6C so that the reaction-liquid received in the measuring cell 5 is sucked and discharged together with the thus introduced rinsing liquid from the liquid discharging pipe 9 through the liquid discharging passage 12.

Thus, when the measurements of reaction-liquids received in the first row of the microcups 2 of the microplate 1 are completed in the direction Y, the microplate 1 is returned its initial position in a direction opposite to its previous transferring direction and then moved in the direction X by the distance P so that measurements of the reaction-liquids received in the second row of the microcups 2 of the microplate 1 are conducted in the same manner as that of the measurements of the first row of the microcups 2. Measurements of the third and the following rows of the microcups 2 are conducted in the same manner as that of the measurements of the first row of the microcups 2.

Since the suction nozzles 6 are provided only in a portion of the disc 3 and further above the disc 3 in the returning movement of the microplate 1, such suction nozzles 6 do not abut against the microplate 1 when the microplate 1 is returned in the direction Y, whereby the returning movement of the microplate 1 is not prevented by the suction nozzles 6.

Figure 4A:
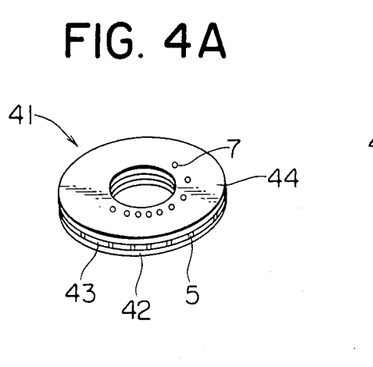
FIG. 4A is a perspective view showing a modification of a disc used in the measuring apparatus of the present invention.
Figure 4B:
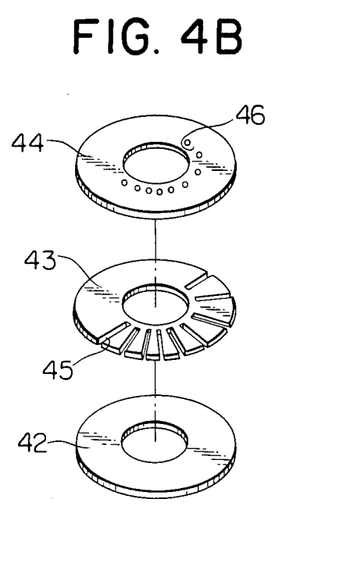
FIG. 4B is a perspective exploded view of the disc shown in FIG. 4A.

FIG. 4A shows an embodiment 41 of the disc (3) before the suction nozzles 6 are mounted thereon. As shown in FIG. 4B, a front disc portion 42, a middle disc portion 43 and a rear disc portion 44, all of which are made of a transparent glass or a transparent plastic material, are piled up in this order to construct the embodiment, i.e., the disc 41. The middle disc portion 43 of the disc 41 may be made of a suitable metal and is radially provided with a predetermined number of slits 45 for forming the plurality of the measuring cells 5, which slits 45 have their openings in an outer periphery of the middle disc portion 43 of the disc 41. The rear disc portion 44 of the disc 41 is provided with a predetermined number of through-holes 46 for forming the plurality of the openings 7, which through-holes 46 are provided in a position communicating with the slits 45 of the middle disc portion 43.

Figure 5A:
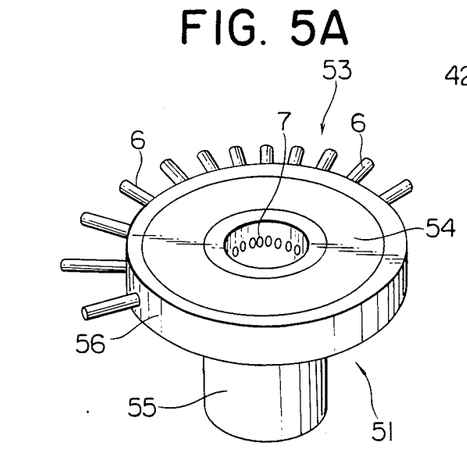
FIG. 5A is a perspective view of another modification of the disc used in the measuring apparatus of the present invention.
Figure 5B:
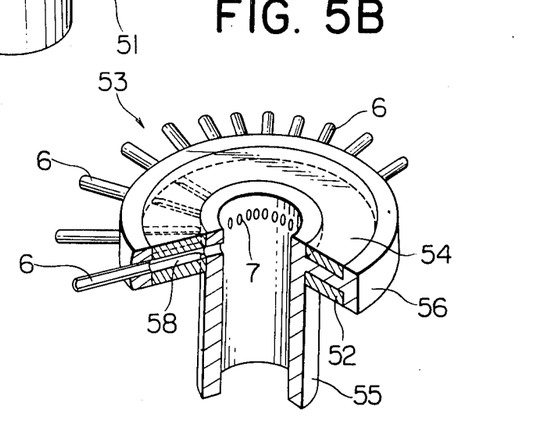
FIG. 5B is a partially cut away perspective view of the another modification of the disc shown in FIG. 5A.
Figure 5C:
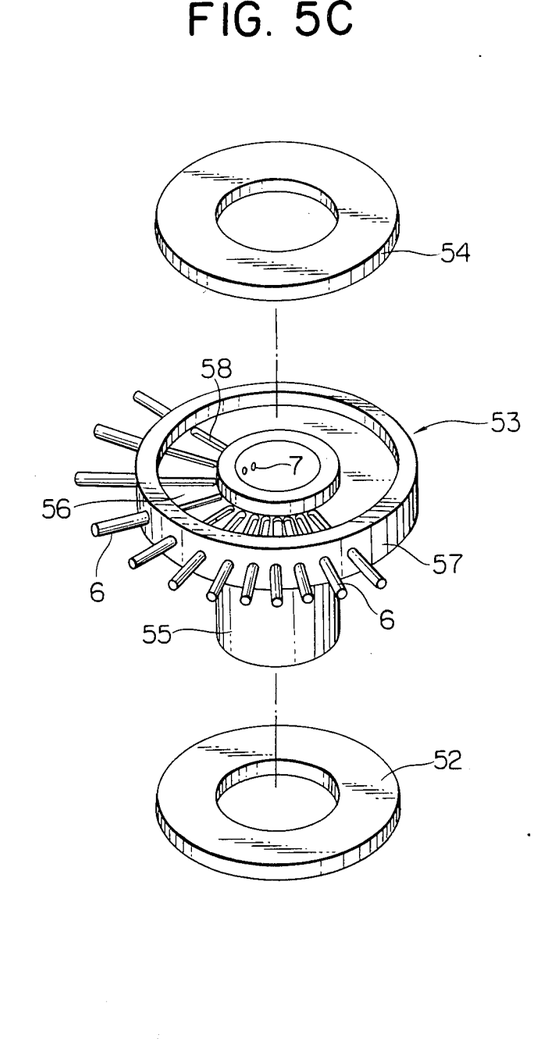
FIG. 5C is an exploded perspective view of the another modification of the disc shown in FIG. 5A.

FIG. 5A shows another embodiment 51 of the disc (3). As shown in FIG. 5C. this embodiment, i.e., the disc 51 is constructed of a front disc portion 52, a middle disc portion 53 and a rear disc portion 54 all of which are made of the transparent glass or transparent plastic material. The middle disc portion 53 may be made of an easy-to-form material such as a metal or a plastic and is provided with: a hollow sleeve-like portion 55; a disc portion 56 radially extending from the vicinity of an end of the sleeve-like portion 55; and a flange portion 57 which is provided in an outer periphery of the disc portion 56 and extends axially in both an upper side and a lower side of the disc portion 56 to form cavities in which the front and rear disc portions 52 and 54 are inserted, respectively. In the disc portion 56, there are provided a predetermined number of slits 58 for forming the measuring cells 5. In the flange portion 57, there are provided the suction nozzles 6 communicating with these slits 58 of the disc portion 56. In the sleeve-like portion 55, there are provided the discharing openings 7 communicating with the slits 58 of the disc portion 56.

Figure 6:
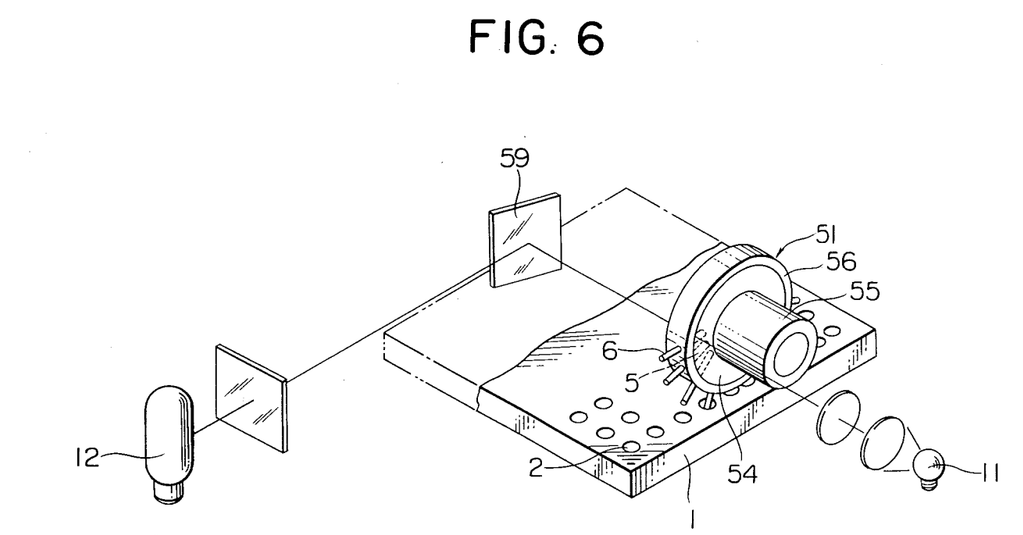
FIG. 6 is a perspective view of the measuring apparatus of the present invention, in which apparatus the disc shown in FIG. 5A is used.

FIG. 6 shows a measuring condition in which the disc 51 is used, wherein a reflecting mirror 59 is interposed between the light source 11 and the light detector 12.

Figure 7:
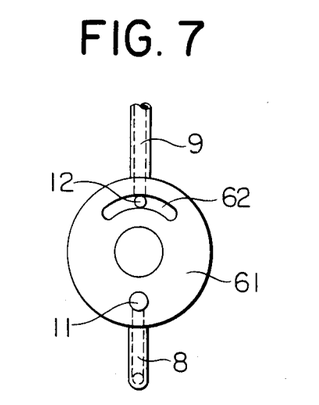
FIG. 7 is a side view of a modification of a supporting plate used in the measuring apparatus of the present invention.

FIG. 7 shows another embodiment 61 of the supporing plate (18). This embodiment, i.e., the supporting plate 61 is provided with an arc-shaped through-hole 62 in its side surface facing the disc 3, which hole 62 communicates with the liquid discharging passage 12. Under the effect of the above construction, the discharging opening 7 communicates with the through-hole 62 of the supporting plate 61 before the measuring cell 5 reaches the rinsing position 5C shown in FIG. 3, so that sucking and discharging actions of the reaction-liquid received in the measuring cell 5 is started just before the rinsing liquid is supplied to the measuring cell 5, and continued while the opening 7 communicates with the through-hole 62 even if the measuring cell 5 is transferred to a position beyond the rinsing position 5C, whereby the discharging action of the reaction-liquid and the rinsing liquid from the measuring cell 5 is sufficiently completed.

Figure 8A:
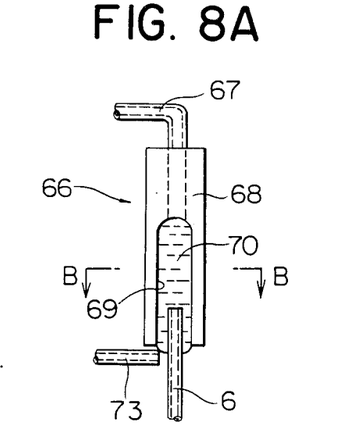
FIG. 8A is a front view of a modification of the rinsing liquid supplying nozzle used in the measuring apparatus of the present invention.
Figure 8B:
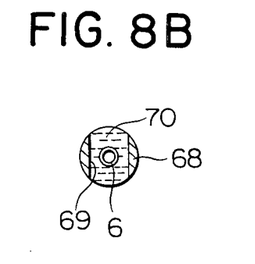
FIG. 8B is a cross sectional view taken along the line B—B of FIG. 8A, shown in a direction of arrows thereof.

FIGS. 8A and 8B show another embodiment 66 of the rinsing liquid supplying pipe (10). This embodiment, i.e., the rinsing liquid supplying pipe 66 is constructed of a rinsing liquid transferring pipe 67 and a supplying head 68 mounted on a front end of the transferring pipe 67, in which supplying head 68 there is provided a slit 69 in a transferring direction of the suction nozzle 6 both the inside and the outside of which are rinsed when the suction nozzle 6 passes through the rinsing liquid 70 retained within the slit 69 under the effect of surface tension of the rinsing liquid 70.

Incidentally, a suction pipe 73 is provided to suction an excess amount of the rinsing liquid 70 in the slit 69 of the supplying head 68.

Figure 9:
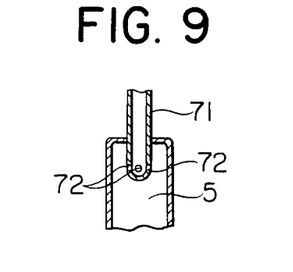
FIG. 9 is a longitudinal sectional view of a modification of the measuring cell and the suction nozzle both used in the measuring apparatus of the present invention.

FIG. 9 shows another embodiment 71 of the suction nozzle (6). This embodiment, i.e., the suction nozzle 71 is mounted on the measuring cell 5 by being inserted in the measuring cell 5 in its closed front end in the vicinity of which a plurality of through-holes 72 are circumferentially provided in a peripheral wall of the suction nozzle 71 at intervals of a suitable distance. For example, as shown in FIG. 8A, since the normal type of the suction nozzle 6 has the opening formed by transversely cutting the front end of the suction nozzle 6, the liquid flows in only one direction so that the reaction-liquid is often transferred directly throuth the plurality of the discharging opening of the measuring cell 5 without being filled in the measuring cell 5 and so taht the rinsing action is not sufficiently conducted. In contrast with this, in the suction nozzle 71, the liquid flows in any directions through the plurality of the through-holes 72, and as a result, the above defect of the suction nozzle 6 is resolved by employing the suction nozzle 71 in place of the suction nozzle 6. These suction nozzles 6, 71 are preferably made of a metal such as a stainless steel or a resilient plastic material.

While the use of the measuring apparatus having the above construction according to the present invention, it is possible to continuously, automatically and optically measure a little amount approximately even 0.2 ml of the reaction-liquid received in the microcup 2 of the microplate 1 by using an accurate length of the optical path of the light beam projected on the measuring cell 5 and the reaction-liquid therein. For example, 96 specimens of the reaction-liquids received in 96 pieces of the microcups 2 each of which has a dismeter of 6 mm and a length of 10 mm can be measured within 2 seconds in case that an amount of each of the 96 specimens is approximately 0.08 ml.

Although the disc 41, 51, are only rotated in the above embodiments of the present invention, it is possible to move them up and down in addition to the above their rotational movements, provided that the suction nozzles 6 are spaced a sufficient distance apart from each other in order to prevent other suction nozzles 6 adjacent to a suction nozzle inserted into the microcup 2 from preventing such inserting movement of the latter nozzle due to their abutting against the microplate 1.

Although particularly preferred embodiments of the present invention have been disclosed in detail for illustrative purpose, it will be recognized that further variations or modifications of the disclosed apparatus, including the rearrangement of parts, lie within the scope of the present invention.

What is claimed is:

1. An optical continuous measuring apparatus for reaction liquid comprising:

a plate-like member provided with a plurality of cavities for receiving a reaction-liquid, said plate-like member being movable in a first direction and a second direction, opposite to said first direction, said cavities being disposed linearly, parallel to said first direction and spaced apart from one another in said first direction by a predetermined uniform distance;

a first dirving means for intermittently moving said plate-like member by said predetermined uniform distance in said first direction;

a disk-shaped rotary member, having front and back side surfaces, a periphery and an axis of rotation transverse to said first direction, provided over said platelike member so as to be rotatable in said first direction;

a plurality of transparent measuring cells receivable of said reaction liquid, each cell having an inlet and an outlet, radially disposed on said rotary member, said inlets being disposed radially outwards of said outlets;

a plurality of suction nozzles projecting radially outward from said rotary member, each suction nozzle corresponding to a respective measuring cell and having a first end and a second end, said second ends being disposed radially inwards of said first ends and being in fluid communication with said inlet of said respective measuring cell, said first ends being circumferentially spaced apart from each other by a distance substantially equal to or slightly greater than said predetermined uniform distance, said first ends being receivable within respective cavities of said plurality of cavities in said plate-like member;

a second driving means for intermittently rotating said rotary member in said first direction such that each of said first ends of said plurality of suction nozzles move a circumferential distance substantially equal to said predetermined uniform distance, said second driving means cooperating with said first driving means so that upon intermittent rotation of said rotary member in said first direction each of said suction nozzles is in turn received within a respective one of said cavities as said plate-like member is intermittently moved in said first direction;

suction means, selectively connectable to said measuring cells, for applying a negative pressure to the outlet of the measuring cell corresponding to the suction nozzle whose first end is received within said respective cavity so as to draw reaction liquid into said measuring cell;

measuring means for optically measuring the reaction liquid received in said measuring cell;

a rinsing liquid supplying/discharging means, connectable to said measuring cells, for supplying a rinsing liquid to said measuring cells and discharging said rinsing liquid from said measuring cells.

2. The optical continuous measuring apparatus for reaction liquid as set forth in claim 1, wherein:

said outlets of said measuring cells individually open to a side surface of said rotary member;

said suction means comprises a suction passage provided in a supporting plate which has a side surface thereof hermetically brought into slidable contact with said backside surface of said rotary member, said suction passage opening, through said side surface of said supporting plate, in a position communicating, in turn, with each of said outlets of said measuring cells upon rotation of said rotary member.

3. The optical continuous measuring apparatus for reaction liquid as set forth in claim 1, wherein:

said rinsing liquid supplying/discharging means comprises a rinsing liquid supply pipe communicable, in turn, with each of said first ends of said suction nozzles upon rotation of said rotary member; and a liquid discharging pipe communicable, in turn, with each of said outlets of said measuring cells upon rotation of said rotary member.

4. The optical continuous measuring apparatus for reaction liquid as set forth in claim 3, wherein said rinsing liquid supply pipe has a front end and a slit formed in said front end, said slit having a width sufficient to enable said first ends of said suction nozzles to pass through said slit, in turn, upon rotation of said rotary member.

5. The optical continuous measuring apparatus for reaction liquid as set forth in claim 3, wherein:

said liquid discharging pipe comprises means defining an opening communicable, in turn, with each of said outlets of said measuring cells upon rotation of said rotary member, said opening means being arc-shaped and formed in a side surface of a supporting member.

6. The optical continuous measuring apparatus for reaction liquid as set forth in claim 1, wherein said plate-like member is further movable in a third direction, which is transverse to said first direction, and a fourth direction, which is opposite to said third direction; and said suction nozzles are provided only on a portion of the outer periphery of said rotary member whereby said plate-like member in its movement in said second, third and fourth directions cooperates with a remaining portion of the outer periphery of said rotary member so that said suction nozzles do not abut against said plate-like member and the plate-like member can be moved free of said suction nozzles.

7. The optical continuous measuring apparatus for reaction liquid as set forth in claim 1, wherein said second ends of said suction nozzles are each received within the inlet of a respective measuring cell, said second ends each being in the form of a hollow closed cylinder having an axis, said second end being provided with a plurality of spaced apart radial through holes in fluid communication with said measuring cell.

* * * * *